United States Patent
Miladinov et al.

(10) Patent No.: US 7,067,156 B1
(45) Date of Patent: Jun. 27, 2006

(54) DIETARY SUPPLEMENT FOR RENAL DIALYSIS PATIENTS

(76) Inventors: Vesselin Danailov Miladinov, 5224 Emmeryville La., Keller, TX (US) 76248; Riccardo Domenico Roscetti, 2221 Cypress Island Dr., Apt. 204, Pompano Beach, FL (US) 33069

( * ) Notice: Subject to any disclaimer, the term of this patent is extended or adjusted under 35 U.S.C. 154(b) by 97 days.

(21) Appl. No.: 10/705,281

(22) Filed: Nov. 10, 2003

(51) Int. Cl.
  *A61K 35/20* (2006.01)
  *A61K 38/00* (2006.01)
  *A23L 1/30* (2006.01)

(52) U.S. Cl. .............................. 424/535; 514/2; 514/9; 426/648; 426/656

(58) Field of Classification Search .................... 514/2, 514/19; 424/535; 426/648, 656
See application file for complete search history.

(56) References Cited

U.S. PATENT DOCUMENTS

| | | | |
|---|---|---|---|
| 5,108,767 A * | 4/1992 | Mulchandani et al. | 426/72 |
| 5,550,106 A * | 8/1996 | Petschow et al. | 514/2 |
| 5,776,887 A * | 7/1998 | Wibert et al. | 514/2 |
| 6,194,379 B1 * | 2/2001 | McEwen et al. | 514/2 |
| 6,288,116 B1 * | 9/2001 | Lowry et al. | 514/565 |
| 6,376,544 B1 * | 4/2002 | Lowry et al. | 514/565 |

* cited by examiner

*Primary Examiner*—Christopher R. Tate
(74) *Attorney, Agent, or Firm*—Gold & Rizvi, P.A.; H. John Rizvi; Glenn E. Gold

(57) ABSTRACT

A dietary supplement which is formulated for medical patients, particularly renal dialysis patients undergoing a peritoneal renal dialysis treatment regimen. The supplement includes a powdered mixture of calcium caseinate, whey protein, L-carnitine and arginine. The ingredients are typically formulated in a powdered form which can be easily added to and ingested with various foods. The supplement provides various nutritional benefits to renal dialysis patients, including the elevation of blood carnitine and albumin levels and the reduction of blood pressure in renal transplant patients.

6 Claims, 1 Drawing Sheet

DIETARY SUPPLEMENT FOR RENAL DIALYSIS PATIENTS

BACKGROUND OF THE INVENTION

1. Field of the Invention

The present invention generally relates to dietary supplements for medical patients, and more particularly, to a dietary supplement which is formulated to meet the specific nutrient demands of renal dialysis patients. The dietary supplement is typically a powdered formulation of calcium casinate, whey protein, L-carnitine and arginine which is added to food to increase the production of albumin in renal dialysis patients.

2. Description of the Prior Art

Every year, about 80,000 people are afflicted with end stage renal disease (ESRD), the final stage of renal failure. In ESRD, the kidneys lose the ability to adequately filter the blood; consequently, wastes accumulate in the body. Several conditions can lead to ESRD, including diabetes and high blood pressure, as well as several other less-common causes. Without medical intervention, ESRD is fatal. Patients with ESRD must either be regularly treated with renal dialysis or receive a kidney transplant to compensate for the loss of kidney function.

Peritoneal renal dialysis is one of the current medical techniques used in the care of patients suffering from renal failure. Peritoneal renal dialysis involves pumping a special fluid into a patient's abdominal cavity. The fluid is balanced in such a manner that waste materials from the blood cross the peritoneal membrane and into the fluid in the peritoneum. The abdominal cavity is then evacuated, with the waste materials removed along with the fluid.

General nutrition guidelines for healthy persons typically stress consumption of large quantities of fruits, vegetables and whole-grain products; moderate quantities of low-fat meat and dairy foods; and low quantities of fat, sugar, alcohol and salt, for optimum health. Patients undergoing peritoneal renal dialysis, however, must follow a restricted diet devoid of meat and low in protein and carnitine. The reductions in protein and carnitine have far-reaching consequences for the patient. For example, a lack of protein in the diet leads to a general state of wasting. Peritoneal renal dialysis patients often experience a reduction of albumin, a major carrier protein in the blood. A reduction of albumin is associated with an increased rate of morbidity and mortality. Consequently, the levels of albumin must be continually monitored in the patient.

Recently, the American Kidney Foundation has increased the recommended levels of albumin from 3.5 g/dl to 4 g/dl. As protein is metabolized by the body, phosphorous is released. Healthy persons have various mechanisms to eliminate excessive quantities of phosphorous from the bloodstream. However, a common problem faced by peritoneal dialysis patients is the lack of ability to remove phosphorous from the blood. The recommended levels of albumin require intake of protein at quantities which may cause accumulation of phosphorous to toxic levels in the blood of such patients.

There is an established need for a dietary supplement which is readily available, formulated to meet the nutritional demands of peritoneal renal dialysis patients and includes calcium to capture phosphorous released from metabolized proteins; carnitine to aid in the restoration and maintenance of carnitine blood levels; and arginine to reduce blood pressure in patients with stable but compromised renal function following renal transplantation.

SUMMARY OF THE INVENTION

The present invention is directed to a dietary supplement which is specifically formulated to meet the nutritional demands of renal dialysis patients and can be added typically in powdered form to a variety of foods, which dietary supplement contains a quantity of protein to equal one ounce of meat; calcium to capture phosphorous released from metabolized protein; carnitine to aid in the restoration and maintenance of blood carnitine levels; and arginine to reduce blood pressure in patients with stable but compromised renal function following transplantation.

An object of the present invention is to provide a dietary supplement that is specifically formulated to meet the nutritional needs of patients undergoing renal dialysis treatment.

Another object of the present invention is to provide a dietary supplement that may be used as an added sole source of nutrition for a renal dialysis patient over an extended period of time.

Still another object of the present invention is to provide a dietary supplement that is provided in an easily digestible form for utilization by renal dialysis patients.

Yet another object of the present invention is to provide a dietary supplement which is particularly suited to patients undergoing peritoneal renal dialysis.

A still further object of the present invention is to provide a dietary supplement that constitutes an ample source of proteins as well as other nutrients such as calcium and is specifically formulated to meet the unique nutritional demands of renal dialysis patients.

These and other objects, features and advantages of the present invention will become more readily apparent from the attached drawings and the detailed description of the preferred embodiments, which follow.

BRIEF DESCRIPTION OF THE DRAWINGS

The invention will be further understood, by way of example, with reference to the accompanying drawing, in which.

DETAILED DESCRIPTION OF THE PREFERRED EMBODIMENTS

Figure 1:
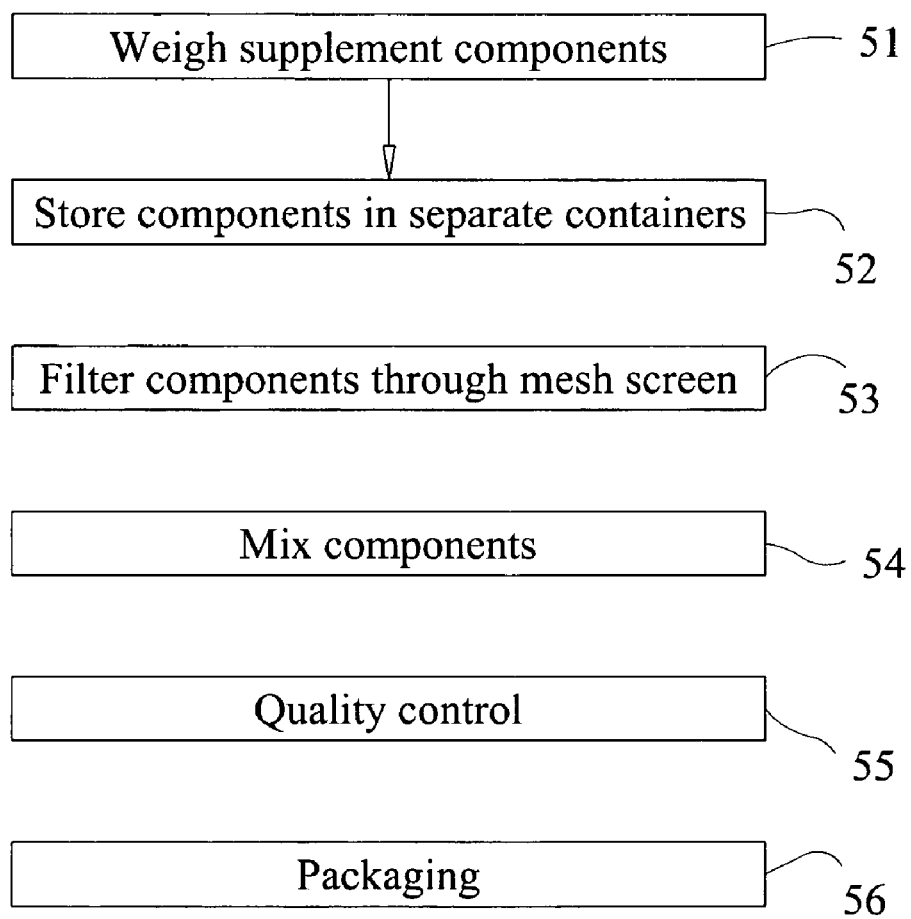
FIG. 1 is a flow diagram illustrating a typical method for synthesizing and packaging the dietary supplement of the present invention.

The present invention comprises a nutrient supplement that is formulated to meet the needs of renal dialysis patients, particularly renal dialysis patients undergoing a peritoneal renal dialysis treatment regimen. The dietary supplement of the present invention provides a complete or nearly complete supply of nutrients which are normally deficient in renal dialysis patients. The supplement is typically formulated in powdered form such that it can be easily added to a patient's meal. For example, the powdered supplement formulation can be mixed and ingested with foods or snacks such as apple sauce, bleached mashed potatoes, broth or soups, in non-exclusive particular.

A typical serving size of the dietary supplement of the present invention is typically about 8 grams. The number of servings to be consumed by a patient per day is typically from about 2 to about 8 per day. Preferably, the number of daily servings is from about 3 to about 5. However, the exact number of servings to be consumed by a patient per day depends on the particular patient and should be determined by a dietitian. Generally, the less other food the patient consumes in his or her diet, the higher quantity of the dietary supplement which will be needed for adequate nutrition.

In a preferred embodiment, the dietary supplement of the present invention includes selected quantities of the following components: calcium caseinate, whey protein, L-carnitine and arginine. The whey protein may be used in powdered form having a concentration of from about 50% to about 100%. The calcium caseinate, L-carnitine and arginine are used as 100% powder.

In a most preferred embodiment, a batch of the dietary supplement of the present invention includes whey protein, L-carnitine and arginine in the following weight ratios with respect to calcium caseinate: whey protein—from about 0.33 to about 2 calcium caseinate:whey protein; L-carnitine—from about 0.05 to about 0.0667 calcium caseinate: L-carnitine; and arginine—from about 0.5 to about 0.667 calcium caseinate:arginine.

A typical batch of the dietary supplement of the present invention is prepared by adding the various components to calcium caseinate in powdered form. Typically, the components are added to about 100 kg of calcium caseinate in the following weight ranges: whey protein—from about 33 kg to about 200 kg; L-carnitine—from about 667 g to about 5 kg; and arginine—from about 6.67 kg to about 50 kg.

Referring to the flow diagram of FIG. 1, a batch of the dietary supplement of the present invention is typically prepared as follows. First, each of the components is weighed in the appropriate proportions for the batch size, as indicated in step S1. Each of the weighed components is typically stored in separate containers, as indicated in step S2. Each of the containers is preferably marked with the name of the component, the weight of the component and the batch number. After all of the components have been sifted through a mesh screen, as indicated in step S3, the powdered components are thoroughly mixed for typically about 30–45 minutes to form a homogenous mixture, as indicated in step S4. After quality control procedures (S5) are carried out, the final mixture is packaged (S6).

The invention will be better understood by reference to the accompanying examples, which are not intended to limit the invention but are for illustrative purposes only.

EXAMPLE 1

Weighing and Labeling

The multiple components corresponding to a 100-kg batch of the dietary supplement of the present invention were prepared for mixing by initially weighing the components and placing the components in 4 (four) separate labeled containers in the following quantities: 71.257 kg of calcium caseinate; 23.515 kg of whey protein; 0.475 kg of L-carnitine; and 4.753 kg of arginine.

EXAMPLE 2

Mixing and Preparation

After all of the components in Example 1 were sifted through a mesh screen, the components were blended in a round blender for 45 minutes to form a homogenous mixture. The dietary supplement composition was then subjected to quality control procedures and packaged.

The following examples illustrate several permissible ranges of the supplement components possible for a batch of the nutritional supplement.

EXAMPLE 3

The multiple components corresponding to a 100-kg batch of the dietary supplement of the present invention were prepared for mixing by initially weighing the components and placing the components in 4 (four) separate labeled containers in the following quantities: 54.447 kg of calcium caseinate; 17.967 kg of whey protein; 0.363 kg of L-carnitine; and 27.223 kg of arginine. These components were then screened, subjected to quality control measures and packaged, according to Example 2.

EXAMPLE 4

The multiple components corresponding to a 100-kg batch of the dietary supplement of the present invention were prepared for mixing by initially weighing the components and placing the components in 4 (four) separate labeled containers in the following quantities: 69.123 kg of calcium caseinate; 22.811 kg of whey protein; 3.456 kg of L-carnitine; and 4.610 kg of arginine. These components were then screened, subjected to quality control measures and packaged, according to Example 2.

EXAMPLE 5

The multiple components corresponding to a 100-kg batch of the dietary supplement of the present invention were prepared for mixing by initially weighing the components and placing the components in 4 (four) separate labeled containers in the following quantities: 53.191 kg of calcium caseinate; 17.553 kg of whey protein; 2.660 kg of L-carnitine; and 26.596 kg of arginine. These components were then screened, subjected to quality control measures and packaged, according to Example 2.

EXAMPLE 6

The multiple components corresponding to a 100-kg batch of the dietary supplement of the present invention were prepared for mixing by initially weighing the components and placing the components in 4 (four) separate labeled containers in the following quantities: 32.538 kg of calcium caseinate; 65.075 kg of whey protein; 0.217 kg of L-carnitine; and 2.170 kg of arginine. These components were then screened, subjected to quality control measures and packaged, according to Example 2.

EXAMPLE 7

The multiple components corresponding to a 100-kg batch of the dietary supplement of the present invention were prepared for mixing by initially weighing the components and placing the components in 4 (four) separate labeled containers in the following quantities: 28.517 kg of calcium caseinate; 57.034 kg of whey protein; 0.190 kg of L-carnitine; and 14.259 kg of arginine. These components were then screened, subjected to quality control measures and packaged, according to Example 2.

EXAMPLE 8

The multiple components corresponding to a 100-kg batch of the dietary supplement of the present invention were prepared for mixing by initially weighing the components and placing the components in 4 (four) separate labeled containers in the following quantities: 32.085 kg of calcium caseinate; 64.171 kg of whey protein; 1.604 kg of L-carnitine; and 2.140 kg of arginine. These components were then screened, subjected to quality control measures and packaged, according to Example 2.

EXAMPLE 9

The multiple components corresponding to a 100-kg batch of the dietary supplement of the present invention were prepared for mixing by initially weighing the components and placing the components in 4 (four) separate labeled containers in the following quantities: 28.169 kg of calcium caseinate; 56.338 kg of whey protein; 1.408 kg of L-carnitine; and 14.085 kg of arginine. These components were then screened, subjected to quality control measures and packaged, according to Example 2.

While the preferred embodiments of the invention have been described above, it will be recognized and understood that various modifications can be made in the invention and the appended claims are intended to cover all such modifications which may fall within the spirit and scope of the invention.

What is claimed is:

1. A dietary supplement comprising:
    a homogenous mixture of calcium caseinate, whey protein, L-carnitine and arginine;
    wherein said calcium caseinate and said arginine are present in said mixture in a weight ratio of from about 0.667 to about 0.5 calcium caseinate:arginine;
    wherein said calcium caseinate and said L-carnitine are present in said mixture in a weight ratio of from about 0.0667 to about 0.05 calcium caseinate:L-carnitine; and
    wherein said calcium caseinate and said whey protein are present in said mixture in a weight ratio of from about 0.33 to about 2 calcium caseinate:whey protein.

2. A dietary supplement comprising:
    a batch consisting of about 100 kg of calcium caseinate, from about 33 kg to about 200 kg of whey protein, from about 667 g to about 5 kg of L-carnitine, and from about 6.67 kg to about 50 kg of arginine.

3. The dietary supplement of claim 2 wherein said calcium caseinate and said whey protein are present in said mixture in a weight ratio of from about 0.33 to about 2 calcium caseinate:whey protein.

4. The dietary supplement of claim 2 wherein said calcium caseinate and said L-carnitine are present in said mixture in a weight ratio of from about 0.0667 to about 0.05 calcium caseinate:L-carnitine.

5. The dietary supplement of claim 2 wherein said calcium caseinate and said arginine are present in said mixture in a weight ratio of from about 0.667 to about 0.5 calcium caseinate:arginine.

6. A method of preparing a dietary supplement, comprising:
    providing calcium caseinate, whey protein, L-carnitine and arginine; and
    forming a homogenous mixture substantially devoid of lipids by mixing said calcium caseinate, said whey protein, said L-carnitine and said arginine;
    wherein said calcium caseinate and said arginine are present in said mixture in a weight ratio of from about 0.667 to about 0.5 calcium caseinate:arginine;
    wherein said calcium caseinate and said L-carnitine are present in said mixture in a weight ratio of from about 0.0667 to about 0.05 calcium caseinate:L-carnitine; and
    wherein said calcium caseinate and said whey protein are present in said mixture in a weight ratio of from about 0.33 to about 2 calcium caseinate:whey protein.

* * * * *